United States Patent [19]
Choi et al.

[11] Patent Number: 5,654,461
[45] Date of Patent: Aug. 5, 1997

[54] SULFAMATE COMPOUND CONTAINING CARBAMOYL GROUP

[75] Inventors: Yong Moon Choi, Towaco, N.J.; Dong Il Han; Hyung Cheol Kim, both of Yusung-ku, Rep. of Korea

[73] Assignee: Yukong Limited, Seoul, Rep. of Korea

[21] Appl. No.: 616,077

[22] Filed: Mar. 14, 1996

[30] Foreign Application Priority Data

Nov. 2, 1995 [KR] Rep. of Korea ............... 1995-39456

[51] Int. Cl.$^6$ ............ C07C 309/63; A61K 31/27; A61K 31/255
[52] U.S. Cl. ............................................. 558/48
[58] Field of Search .................. 558/48; 514/517

[56] References Cited

U.S. PATENT DOCUMENTS

| | | | |
|---|---|---|---|
| 4,792,569 | 12/1988 | Maryanoff et al. | 514/517 |
| 5,384,327 | 1/1995 | Costanzo et al. | 514/456 |
| 5,510,379 | 4/1996 | Lee et al. | 514/517 |

OTHER PUBLICATIONS

Maryanoff et al., "Anticonvulsant O-Alkyl Sulfamates, etc.", J. Med. Chem., 30, 880–887. 1987.

*Primary Examiner*—Peter O'Sullivan
*Attorney, Agent, or Firm*—Abelman, Frayne & Schwab

[57] ABSTRACT

3-O-Carbamoyl-2-phenyl-1,3-propanediol sulfamate racemate, represented by the following structural formula I:

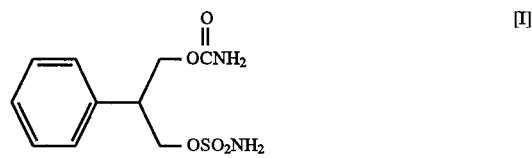

and its (R)- and (S)-optical isomers, which are very effective for prophylaxis and the treatment of central nervous system disorders including nervous muscular pain, epilepsy and minimal brain dysfunctions, are disclosed. They are prepared from 2-phenyl-1,3-propanediol monocarbamate and its optical isomers, respectively.

3 Claims, No Drawings

SULFAMATE COMPOUND CONTAINING CARBAMOYL GROUP

BACKGROUND OF THE INVENTION

1. Field of the Invention

The present invention relates to sulfamate compounds derived from 2-phenyl-1,3-propanediol monocarbamate. More particularly, the present invention is concerned with 3-O-carbamoyl-2-phenyl-1,3-propanediol sulfamates including their racemates and (R)- and (S)-optical isomers, useful for prophylaxis and treatment of the disorders of the central nervous system.

2. Description of the Prior Art

Many reports have disclosed and illustrated that sulfamate compounds are effectively used as medicines for controlling various central nervous system (CNS) disorders, especially for an epilepsy.

As a prior art relating to these compounds, fructopyranose sulfamate compounds are reported in J. Med. Chem. 30, 880–887(1987), together with their pharmaceutical effects. Other pharmaceutically useful sulfamates, for example, sorbopyranose sulfamate and penethylsulfamate are disclosed in PCT WO 14827 and U.S. Pat. No. 4,792,569, respectively.

These compounds have effectively been used as therapeutical medicines for managing CNS diseases, such as an antiepileptic. Active research and development efforts have been and continue to be directed to the application of sulfamate compounds for CNS disorders.

SUMMARY OF THE INVENTION

As a result of intensive and thorough research for the derivatives of 2-phenyl-1,3-propanediol monocarbamate, the present inventors found that sulfamoyl-introduced carbamates are pharmaceutically useful in prophylaxis and treatment of CNS disorders, especially, epilepsy.

In vivo, an optical isomer of one compound may exhibit an even better pharmaceutical effect than other optical isomers, and many examples of the optical effect have been reported. The recent trend is to use optical isomers to develop new medicines. Thus, it is very important to resolve the racemic mixture of one compound into respective optical isomers and apply them for pharmacology.

Accordingly, it is an object of the present invention to provide novel carbamoyl-containing sulfamate compounds effective for prophylaxis and the treatment of CNS disorders.

In accordance with the present invention, there are provided novel sulfamate compounds, 3-O-carbamoyl-2-phenyl-1,3-propanediol sulfamate, represented by the following structural formula I:

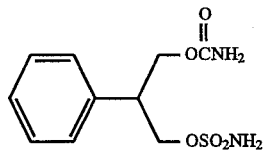

(R)-3-O-carbamoyl-2-phenyl-1,3-propanediol sulfamate, represented by the following structural formula II:

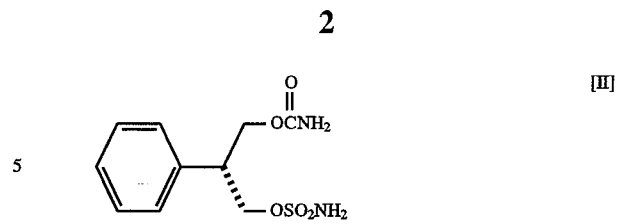

and (S)-3-O-carbamoyl-2-phenyl-1,3-propanediol sulfamate, represented by the following structural formula III:

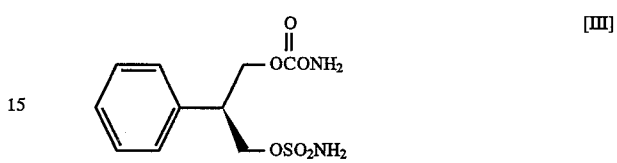

which all exhibit high pharmacological efficacy for prophylaxis and treatment of CNS disorders.

DETAILED DESCRIPTION OF THE INVENTION

The novel compound of the structural formula I is a chiral molecule with a chiral center of carbon at benzyl and may have either (R)- or (S)-configuration.

According to the present invention, 3-O-carbamoyl-2-phenyl-1,3-propanediol sulfamate racemate of the structural formula I can be prepared by reacting 2-phenyl-1,3-propanediol monocarbamate represented by the following structural formula IV:

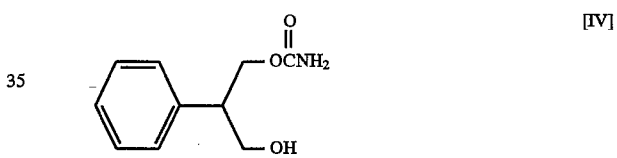

as a starting material with sulfamoyl chloride in a suitable solvent in the presence of a base catalyst.

For the solvent, an amide such as dimethylformamide, an ether such as ethylether and tetrahydrofuran, or acetonitrile is available. Preferred is ethylether, tetrahydrofuran or acetonitrile.

As the base catalyst, an amine compound, such as triethyl amine, pyridine and antipyrine, is recommended.

When 2-phenyl-1,3-propanediol monocarbamate, the starting material, is used at an amount of about 0.01 to 2.0 moles, sulfamoyl chloride necessary for the reaction is used at about 1.0 to 3.0 equivalents with the base catalyst of 1.0 to 2.0 equivalents. Reaction temperature is selected from a range of −10° to 30 ° C.

Likewise, (R)-3-O-carbamoyl-2-phenyl-1,3-propanediol sulfamate of the structural formula II is prepared from (S)-2-phenyl-1,3-propanediol monocarbamate represented by the following structural formula V:

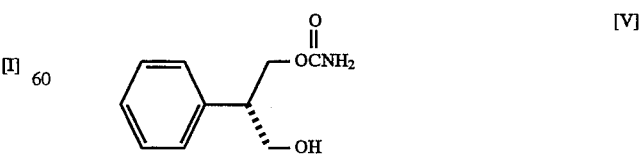

This preparation can be done by reacting (S)-2-phenyl-1,3-propanediol monocarbamate with sulfamoyl chloride in a solvent at a temperature of −10° to 30° C. in the presence of a base catalyst, in accordance with the present invention.

Examples of useful solvent include an amide such as dimethylformamide, an ether such as ethylether and tetrahydrofuran and acetonitrile with a preference of ethylether, tetrahydrofuran and acetonitrile.

The same catalyst as that for the reaction of the racemate can be employed including triethyl amine, pyridine and antipyrine.

As for the amounts of the reaction components in this optically specific reaction, (S)-2-phenyl-1,3-propanediol monocarbamate, the starting material is used at an amount of about 0.01 to 2.0 moles with 1.0 to 3.0 equivalents of sulfamoyl chloride and 1.0 to 2.0 equivalents of the base catalyst.

Similarily, (S)-3-O-carbamoyl-2-phenyl-1,3-propanediol sulfamate of the structural formula III can be prepared by reacting 2-phenyl-1,3-propanediol monocarbamate represented by the following structural formula VI:

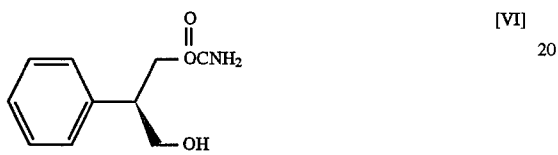

as a starting material with sulfamoyl chloride in a suitable solvent in the presence of a base catalyst.

For the solvent, the same solvent as used for the preparation of the above compounds of structural formulas I and II is available.

As the base catalyst, an amine compound, such as triethyl amine, pyridine and antipyrine, is recommended.

When (R)-2-phenyl-1,3-propanediol monocarbamate, the starting material, is used at an amount of about 0.01 to 2.0 moles, sulfamoyl chloride necessary for the reaction is used at about 1.0 to 3.0 equivalents with the base catalyst of 1.0 to 2.0 equivalents. Reaction temperature is selected from a range of −10° to 30° C.

The sulfamate compounds as above are found to be very effective for the prophylaxis and treatment of CNS disorders.

A better understanding of the present invention may be obtained in light of following examples which are set forth to illustrate, but are not to be construed to limit, the present invention.

EXAMPLE I

Preparation of 3-O-Carbamoyl-2-phenyl-1,3-propanediol sulfamate

A well dry 500 mL flask equipped with a thermometer was purged with nitrogen gas, to completely remove moisture and air from the inside of the flask. This purging continued for 30 min. Thereafter, 5 g of 2-phenyl-1,3-propanediol monocarbamate and 4.05 ml of pyridine were well dissolved in 150 ml of purified acetonitrile. The solution was fed into the flask and made to be homogeneous by stirring for 30 min. While being maintained at 0° C., the homogeneous solution was slowly added with 4.44 g of sulfamoyl chloride.

Reaction was executed at the same temperature under double monitoring of thin layer chromatography and liquid chromatography by which the termination of reaction was determined. Roughly, it took about 4 hours to finish the reaction.

After completion of the reaction, acetonitrile used as the solvent was removed by a rotary evaporator. The residue was fractioned with 30 ml of distilled water and 30 ml of ethyl acetate. The organic layer was extracted, dried over anhydrous magnesium sulfate and distilled off ethyl acetate by a rotary evaporator, to give a yellow liquid.

This concentrated liquid mixture was separated by column chromatography using as a mobile phase a mixture of ethyl acetate/n-hexane (2:1), to obtain 4.49 g of 3-O-carbamoyl-2-phenyl-1,3-propanediol sulfamate.

Sulfamoyl chloride which is used at this reaction had been synthesized by the Appel and Berger's method disclosed in Chem. Ber., 91, 1339–1341 (1958).

Yield: 64%

$^1$H-NMR(CDCl$_3$, 200 MHz), ppm (δ): 3.20–3.45(m,1H), 4.21–4.25(d,2H), 4.26–4.34(d,2H), 4.95(br,2H), 5.50(br, 2H), 7.12–7.30(m,5H)

EXAMPLE II

Preparation of (R)-3-O-Carbamoyl-2-phenyl-1,3-propanediol sulfamate

A well dry 500 mL flask equipped with a thermometer was purged with nitrogen gas, to completely remove moisture and air from the inside of the flask. This purging continued for 30 min. Thereafter, 5 g of (S)-2-phenyl-1,3-propanediol monocarbamate and 4.05 ml of pyridine were well dissolved in 150 ml of purified acetonitrile. The solution was fed into the flask and made to be homogeneous by stirring for 30 min. While being maintained at 0° C., the homogeneous solution was slowly added with 4.44 g of sulfamoyl chloride.

Reaction was executed at the same temperature under double monitoring of thin layer chromatography and liquid chromatography by which the termination of reaction was determined. Roughly, it took about 4 hours to finish the reaction.

After completion of the reaction, acetonitrile used as the solvent was removed by a rotary evaporator. The residue was fractioned with 30 ml of distilled water and 30 ml of ethyl acetate. The organic layer was extracted, dried over anhydrous magnesium sulfate and distilled off ethyl acetate by a rotary evaporator, to give a yellow liquid.

This concentrated liquid mixture was separated by column chromatography using as a mobile phase a mixture of ethyl acetate/n-hexane (2:1), to obtain 4.21 g of (R)-3-O-carbamoyl-2-phenyl-1,3-propanediol sulfamate.

Yield: 60%

$^1$H-NMR(CDCl$_3$, 200 MHz), ppm (δ): 3.20–3.45(m,1H), 4.21–4.25(d,2H), 4.26–4.34(d,2H), 4.95(br,2H), 5.50(br, 2H), 7.12–7.30(m,5H)

EXAMPLE III

Preparation of (S)-3-O-Carbamoyl-2-phenyl-1,3-propanediol sulfamate

A well dry 500 mL flask equipped with a thermometer was purged with nitrogen gas, to completely remove moisture and air from the inside of the flask. This purging continued for 30 min. Thereafter, 5 g of (R)-2-phenyl-1,3-propanediol monocarbamate and 4.05 ml of pyridine were well dissolved in 150 ml of purified acetonitrile. The solution was fed into the flask and made to be homogeneous by stirring for 30 min. While being maintained at 0° C., the homogeneous solution was slowly added with 4.44 g of sulfamoyl chloride.

Reaction was executed at the same temperature under double monitoring of thin layer chromatography and liquid chromatography by which the termination of reaction was determined. Roughly, it took about 4 hours to finish the reaction.

After completion of the reaction, acetonitrile used as the solvent was removed by a rotary evaporator. The residue was fractioned with 30 ml of distilled water and 30 ml of ethyl acetate. The organic layer was extracted, dried over anhydrous magnesium sulfate and distilled off ethyl acetate by a rotary evaporator, to give a yellow liquid.

This concentrated liquid mixture was separated by column chromatography using as a mobile phase a mixture of ethyl acetate/n-hexane (2:1), to obtain 4.70 g of (S)-3-O-carbamoyl-2-phenyl-1,3-propanediol sulfamate.

Yield: 67%

$^1$H-NMR(CDCl$_3$, 200 MHz), ppm (δ): 3.20–3.45(m,1H), 4.21–4.25(d,2H), 4.26–4.34(d,2H), 4.95(br,2H), 5.50(br, 2H), 7.12–7.30(m,5H)

The sulfamate compounds prepared in Examples I to III were identified to be very effective for the prophylaxis and treatment of CNS diseases, such as nervous muscular pain, epilepsy and minimal brain dysfunction.

The present invention has been described in an illustrative manner, and it is to be understood that the terminology used is intended to be in the nature of description rather than of limitation.

Many modifications and variations of the present invention are possible in light of the above teachings. Therefore, it is to be understood that within the scope of the appended claims, the invention may be practiced otherwise than as specifically described.

What is claimed is:

1. 3-O-Carbamoyl-2-phenyl-1,3-propanediol sulfamate, represented by the following structural formula I:

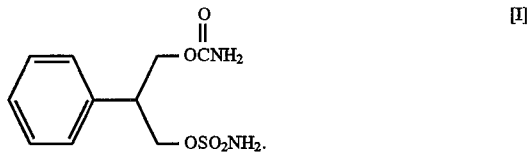

2. (R)-3-O-Carbamoyl-2-phenyl-1,3-propanediol sulfamate, represented by the following structural formula II:

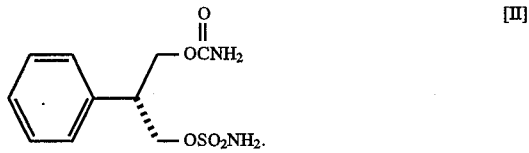

3. (S)-3-O-Carbamoyl-2-phenyl-1,3-propanediol sulfamate, represented by the following structural formula III:

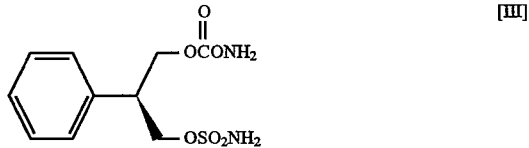

* * * * *